(12) United States Patent
Glazier et al.

(10) Patent No.: US 7,724,373 B2
(45) Date of Patent: May 25, 2010

(54) SUB-MICRON SURFACE PLASMON RESONANCE SENSOR SYSTEMS

(75) Inventors: James A. Glazier, Bloomington, IN (US); Bogdan Dragnea, Bloomington, IN (US); Dragos Amarie, Bloomington, IN (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 381 days.

(21) Appl. No.: 11/611,509

(22) Filed: Dec. 15, 2006

(65) Prior Publication Data

US 2007/0153284 A1   Jul. 5, 2007

Related U.S. Application Data

(60) Provisional application No. 60/750,872, filed on Dec. 16, 2005.

(51) Int. Cl.
*G01N 21/55*    (2006.01)
(52) U.S. Cl. ...................................................... 356/445
(58) Field of Classification Search .......... 356/445–448
See application file for complete search history.

(56) References Cited

U.S. PATENT DOCUMENTS

| | | | |
|---|---|---|---|
| 5,395,587 A | 3/1995 | Brigham-Burke et al. |
| 5,606,633 A | 2/1997 | Groger et al. |
| 5,858,195 A | 1/1999 | Ramsey |
| 5,986,808 A | 11/1999 | Wang |
| 6,208,883 B1 | 3/2001 | Holupka et al. |
| 6,375,871 B1 | 4/2002 | Bentsen et al. |
| 6,480,282 B1 | 11/2002 | Chinowsky et al. |
| 6,579,721 B1 | 6/2003 | Natan et al. |
| 6,592,519 B1 | 7/2003 | Martinez |
| 6,660,381 B2 | 12/2003 | Halas et al. |
| 6,801,317 B2 | 10/2004 | Hofmann |
| 6,835,534 B2 | 12/2004 | Weiss et al. |
| 6,947,145 B2 | 9/2005 | Naya |
| 6,956,651 B2 | 10/2005 | Lackritz et al. |
| 7,074,621 B2 | 7/2006 | Latov et al. |
| 7,118,710 B2 | 10/2006 | Cunningham |
| 7,129,096 B2 | 10/2006 | Chilkoti et al. |
| 7,142,296 B2 | 11/2006 | Cunningham et al. |
| 2002/0187074 A1 | 12/2002 | O'Connor et al. |
| 2003/0059820 A1 | 3/2003 | Vo-Dinh |
| 2003/0231304 A1 | 12/2003 | Chan et al. |

(Continued)

OTHER PUBLICATIONS

Rice, Todd W., and Bernard, Gordon R., "Therapeutic Intervention and Targets for Sepsis", Annu. Rev. Med. 2005, vol. 56, pp. 225-248.

(Continued)

*Primary Examiner*—Hoa Q Pham
(74) *Attorney, Agent, or Firm*—Barnes & Thornburg LLP

(57) ABSTRACT

A sensor for detecting the presence of a target analyte, ligand or molecule in a test fluid, comprising a light transmissive substrate on which an array of surface plasmon resonant (SPR) elements is mounted is described. A multi-channel sensor for detecting the presence of several targets with a single micro-chip sensor is described. A multi-channel sensor including collections of SPR elements which are commonly functionalized to one of several targets is also described. The detectors sense changes in the resonant response of the SPR elements indicative of binding with the targets.

11 Claims, 7 Drawing Sheets

U.S. PATENT DOCUMENTS

| | | | |
|---|---|---|---|
| 2004/0238484 | A1 | 12/2004 | Le Pioufle et al. |
| 2006/0134704 | A1 | 6/2006 | Muraguchi et al. |
| 2006/0246510 | A1 | 11/2006 | Densham |
| 2008/0088845 | A1* | 4/2008 | Ke et al. ............... 356/445 |
| 2008/0264151 | A1* | 10/2008 | Sullivan et al. .......... 73/64.47 |
| 2009/0073447 | A1* | 3/2009 | Dahint et al. ........... 356/445 |

OTHER PUBLICATIONS

Karlsson, Robert and Stahlberg, Ralph, "Surface Plasmon Resonance Detection and Multispot Sensing for Direct Monitoring of Interactions Involving Low-Molecular-Weight Analytes and for Determination of Low Affinities", Analytical Biochemistry, 228, pp. 274-280, 1995.

Endo, Tatsuro et al., "Label-Free Detection of Peptide Nucleic Acid-DNA Hybridization Using Localized Surface Plasmon Resonance Based Optical Biosensor", Analytical Chemistry, vol. 77, No. 21, Nov. 1, 2005, 9 pages.

New Scientist, Nov. 5, 2005, www/.newscientist.com, pp. 1.

Endo, Tatsure et al., "Multiple Label-Free Detection of Antigen-Antibody Reaction Using Localized Surface Plasmon Resonance-Based Core-Shell Structured Nanoparticle Layer Nanochip", Anal. Chem. 2006, vol. 78, No. 18, Sep. 15, 2006, 11 pages.

Hutter, Eliza and Fendler, Janos H., "Exploitation of Localized Surface Plasmon Resonance", Adv. Matr. vol. 16, No. 19, Oct. 4, 2004, 21 pages.

* cited by examiner

SUB-MICRON SURFACE PLASMON RESONANCE SENSOR SYSTEMS

CROSS-REFERENCE TO RELATED APPLICATION

This application claims priority to provisional application No. 60/750,872, filed on Dec. 16, 2005, entitled "Sub-micron Cavity Surface Plasmon Sensors and Their Micro-fluidic Applications", the entire disclosure of which is incorporated by reference herein.

GOVERNMENTAL INTEREST

Part of the work during the development of this invention was made with government support from the National Science Foundation under grant number IBM-0083653 and from NASA under grant number NAG2-1619. Pursuant to these grants, the U.S. Government has certain rights in the invention disclosed herein.

BACKGROUND

A significant trend in medicine is the introduction of point of care (POC) devices for rapid, bedside diagnosis. These devices enable rapid diagnosis by first responders or medical staff for time-critical diagnoses, such as for indicating whether patients are presenting with cardiac symptoms. Tests have been developed for other indications, such as infectious diseases, drugs of abuse, cerebrovascular disease, that are intended to circumvent the lengthy processing hours and high costs accompanying conventional in-house laboratory assays. Current POC devices are single use only. While this is suitable for many applications, there is an unmet need for continuous monitoring devices.

An initial clinical need is a device that can monitor and detect the presence of infections in intensive care patients. Currently, many intensive care patients develop infections that are not detected quickly, often leading to sepsis or shock and resulting in a large mortality rate. There is a significant need for a device that can continuously track the concentration of specific protein markers in a patient's bloodstream that are indicative of an infection, for instance.

Devices that are capable of detecting the presence of selected chemicals or biological substances include biosensors that interact directly with a sample molecule to provide a signal identifying the test molecule. Biosensors are often functionalized chemically to make them selective. The readout can be electrochemical, as is often the case for small molecules (e.g. glucose), or can utilize fluorescence or other optical techniques for molecules such as proteins or DNA. Typical biosensors can often operate in a continuous reading mode or can be used multiple times, which differs from conventional laboratory assays requiring bulk reagent handling, usually yielding only a one-time test result.

The miniaturization possibilities afforded by biosensors compared to conventional laboratory assays suggests that point of care (POC) tests could provide dramatically enhanced diagnostic capabilities. The benefits of POC testing include: rapid turnaround which aids therapeutic decisions; quick dissemination of test results to patients, thereby reducing physician workload and increasing patient satisfaction; reduced paper work and simplified sample tracking; and reduced need for specialized technicians. POC tests administered as panels provide further significant benefits. For example, screening for several cardiac markers simultaneously saves time and provides useful additional data. Screens for various types of influenza would aid diagnosis compared to more limited tests on only single strains.

Emerging applications of biosensors include food and water testing, drugs of abuse, bio-defense and "white powder" detection, and veterinary testing, to name a few. Some of these applications have unique needs such as the need for ultra-fast response time in conjunction with bio-defense measures, or high sensitivity necessary in food or water testing to detect a very low number of *E. Coli* colony-forming units. Typical water testing products use reagents that must be incubated in flasks for 18-24 hours or longer, changing color to indicate pathogen presence. While these products are very effective, the lengthy, 24 hour incubation time can be problematic. When the contaminated water is in a public drinking supply, the water may be in use for extended periods before a pathogen problem is detected. A product that continuously monitors water quality can provide a warning within minutes of actual contamination.

Bio-defense presents unique issues as governmental and military agencies search for ways to rapidly and interactively detect anthrax, botulism, malaria, Ebola virus, ricin, and other potential terrorist agents. Expensive test kits are currently used by the US Postal Service that incorporate real-time PCR to amplify and analyze crude samples obtained from air or suspicious "white powder" on packages and envelopes.

A new breed of biosensors utilizes a phenomenon arising from the interaction of light with a metal surface. This phenomenon is called "surface plasmon resonance" and embodies a charge-density (electron cloud) oscillation that may exist at the interface of two media with different dielectric constants or dielectric constants of opposite signs. This condition is usually met at the interface between a dielectric (glass) and a metal (typically gold or silver). The charge density wave (the electron cloud) is associated with an electromagnetic wave (the incoming photons), and this coupling reaches a maxima at the interface and decays exponentially into both media. This coupling is, in effect, a surface bound plasma wave (SPW).

This coupling cannot be excited directly by incident optical photons at a planar metal-dielectric interface because the propagation constant of an SPW is always higher than that of the wave propagating in the dielectric. Therefore to enhance this coupling, attenuated total reflection (ATR), prism couplers and optical waveguides, or diffraction at the surface of diffraction gratings is used. As the excitation of SPWs by optical photons results in resonant transfer of energy into the SPW, surface plasmon resonance (SPR) manifests itself by resonant absorption of the energy of the optical photons. Owing to the strong concentration of the electromagnetic field in the dielectric (an order of magnitude higher than that in typical evanescent field sensors using dielectric waveguides) the propagation constant of the SPW, and consequently the SPR formation, is very sensitive to variations in the optical properties of the dielectric adjacent to the metal layer supporting SPW, namely the refractive index of the dielectric media which may be determined by optically interrogating the SPR. The thickness of the region of sensitivity varies with the wavelength off the applied energy, but is typically about 500 nm for wavelengths in the visible light range. The refractive index is modified by the presence of materials or impurities at the surface. This is the fundamental effect that can be used to identify the materials or impurities with great precision.

Metals are materials that can provide the negative sign dielectric constant. They have a resonant mode at which the constituent electrons resonate when excited by electromagnetic radiation having the right wavelength. Gold, in particular, has a spectrum with a resonance at visible wavelengths around 510 nm. In the case of the attenuated total reflection in prism couplers, the evanescent wave is sensitive to the metal surface in contact with the media within approximately 200-400 nm of the surface, enhanced by the presence of a surface plasmon wave. Such material effectively modifies the index of refraction and thus the precise angle of critical attenuated total reflection. Interactions between a bound substrate and a sample can thus be probed, measuring small variations in the reflection angle at maximum SPR production.

This effect can be harnessed to study binding between molecules, such as between proteins, RNA and/or DNA, or between proteins and viruses or bacteria. For example, a surface functionalized with a specific antibody will probe for only one antigen (e.g. antigen A) and discriminate specific binding from non-specific binding. That is, antigen A will be detected but weaker interactions between the functionalized protein bound to the surface and another antigen, say antigen B, can be distinguished. Typically, angular resolution of a few millidegrees is required to discriminate between selective and non-selective binding. Thus the detection of protein A in solution as dilute as 1 pg/ml may be achieved. In addition, the reaction kinetics of the binding between the surface protein and antigen A can be elucidated.

Most commercial SPR instruments comprise a sample introduction device or sensor that includes a semispherical dielectric prism coated with a thin layer (50 nm) of a noble metal such as Au or Ag. This metal coating in turn is coated with molecules that will specifically bind a target analyte. These commercial devices further comprise a light source on a goniometric mount, an array detector, and various collimation and filtering optics, as depicted generally in FIG. 1.

Using a semispherical prism, the angle of incidence at the dielectric/air interface is the same as at the first air/dielectric interface where the ray from the light source enters the prism. At the precise incidence angle at which light couples to a non-radiative evanescent wave (surface plasmon) in the metal film, the reflectivity of the film decreases roughly 90% creating an evanescent plasmon field which is localized at the metal surface away from the glass. The evanescent wave's properties depend on the properties of the medium (e.g., biomolecules) in contact with the free metal surface of the sensor. Subtle changes in the refractive index of the medium, such as those associated with molecular absorption onto the surface, induce detectable changes in the surface plasmon resonance angle $\phi$. The SPR instrument then adjusts the detector position to find this new angle and thus measures the change in SPR angle.

These types of SPR devices have a number of inherent limitations involving sensitivity, sample size, complexity, and cost. Existing commercial instruments require large, complex, and delicate moving parts in order to optimize the incident beam and detector positions. For instance, the goniometric mount for the light source is relatively big and heavy, but delicate. Moreover, the light source itself must provide polarized light. Typical sensitivity limits are on the order of $10^{-6}$ refractive index units which is usually sufficient to detect targets with a concentration of 1 pg/mm$^2$ of adsorbed molecule and a size of at least 200 Da, but is not sensitive enough to provide useful detection for bio-terrorism agents in concentrations of 0.01 parts per billion as required by certain government standards. The typical planar sensor footprint is in the range of a few mm$^2$ ($1/16^{th}$ mm$^2$ in the Biacore Flexichip and 2.2 mm$^2$ in the Biacore 3000) which creates a technical constraint on the ability to miniaturize these sensors. A larger sensor area means that more test fluid must be provided to flow over the planar sensor. Moreover, the constraints on accuracy also require more test fluid to provide sufficient molecules or microparticles to be detected. Because of an SPR sensor's macroscopic size, arrays of sensing elements for multiplexed analysis require sample volumes too large for most technologies used for analytical integration. All of these limitations of conventional planar sensors reduce the throughput capability of the sensors.

Additionally, most current SPR sensors require p-polarized light (i.e., the electric vector component is parallel to the plane of incidence) and precise alignment of their optical parts, which are comparable in complexity to those of a tabletop spectrometer. This results in high cost, typically on the order of several hundred thousand dollars.

SUMMARY OF THE INVENTION

Figure 1:
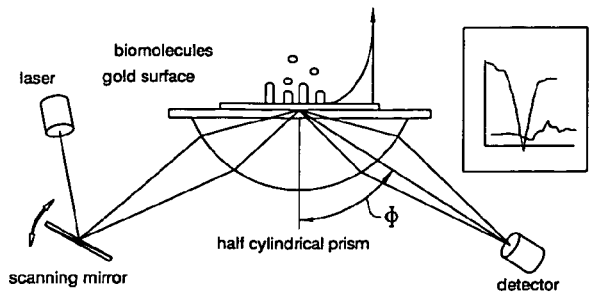
FIG. 1 is a schematic representation of the operation of a flat-substrate SPR sensor of the prior art.

Evanescent-wave sensors using SPR techniques for biomolecular interaction analysis, for instance, provide several advantages, including non-intrusiveness, real-time monitoring of the binding of target analytes, ligands or molecules and label-free conditions. A mechanism to increase the sensitivity of SPR sensors while reducing the size of the sensor would be very desirable, especially in the fields of medical diagnostics, drug screening, biomedical research, and bioanalysis. Another desirable goal is to eliminate the often fragile mechanical and optical components that add bulk to the sensor, increase response time and decrease sensitivity. In accordance with one aspect of the present invention, the propagating plasmon wave is replaced with a stationary wave or, in other words, the sensitivity of the SPR sensor is enhanced by adding shape resonance. Such a stationary wave will travel across the active surface a number of times proportional to the quality factor of the resonance, thus increasing the probability of interaction between the wave and the binding agent.

The circulation of light within highly symmetric microscopic structures often involves such shape resonances. For dielectric spheres 10-100 μm in size, a particular class of resonances occurs known as whispering gallery modes. The term stems from similarities with the phenomenon of circumferential guiding of faint sounds along the walls of the gallery of St. Paul's Cathedral in London. Bioanalytical and spectroscopic applications can take advantage of the characteristic of strong surface localization and high quality factors of whispering gallery modes in dielectric microspheres and liquid droplets. However, the whispering gallery modes gradually lose their surface localization properties as the microsphere size decreases, generally rendering whispering gallery modes ineffective in a microsphere environment.

For submicron sizes (i.e., less than 1 μm in diameter), one way to maintain light confinement is to coat the sphere with a surface plasmon (SP) supporting metal film. One characteristic of such a microsphere coated with a metal film is that at certain diameters the total internal reflection angles associated with cavity modes may coincide with the SPR Angle for the metal film, thus resulting in a more efficient form of SP excitation on geometrically symmetric surfaces. This feature eliminates the need for the polarized light source, optical alignment and mechanical scanning found in prior sensors, and allows relaxation of the stringent geometric conditions imposed on planar sensors.

The present invention comprises a novel sensor that may be optimally used in combination with micro-fluidic systems. Measurements of (bio)chemical concentrations and kinetics of reactions inside a confined space such as a micro-fluidic device are very difficult. The present invention contemplates a submicron dielectric bead covered with a metal which supports surface plasmons, e.g. Au, Ag, Cu. This SPR shows a strong enhancement in transmission of certain wavelengths due to the periodic boundary conditions created by the geometry of the sensor element coupled with surface plasmons induced in the metal shell. This inventive sensor is sensitive to small changes of the refractive index of the material at the very surface of the sensor (i.e., within about 300 nm) and is much more sensitive than prior far-field sensors and detection techniques.

Thus, the present invention contemplates a micro-cavity device that utilizes surface plasmon resonance enhanced by geometric or shape resonances. For the purposes of the present disclosure, this device will be referred to herein as a Micro-cavity Surface Plasmon Resonance (MSPR) sensor. In the following description, a spherical cavity resonator has been selected, but it is understood that other symmetric geometric shapes may be used that are capable of sustaining boundary conditions for the stationary plasmon resonance wave to travel across the active surface.

Thus, in one aspect of the invention, the MSPR replaces the propagating plasmon wave associated with traditional SPR sensors with a stationary wave that travels across the active surface of the sensor element. In order to achieve this near-field coupling the dielectric cavity resonator is coated with an SPR-supporting metal of a particular thickness. This metal layer, together with the refractive index of the cavity resonator material, establishes a resonant frequency (or frequencies) for the cavity resonator sensor element. The dimension of the sensor element is then determined in relation to this resonant frequency. In particular, in one aspect, the sensor element is sized at about the wavelength of the resonant frequency.

In accordance with the invention, the sensor element or bead is mounted on a light transmissive substrate, such as glass. The substrate and the bead are coated with an SPR-supporting material, such as gold. In a further feature of the invention, a pinhole is defined at the interface between the bead and the substrate which is free of the coating material. The size of this pinhole is also calibrated to the resonant wavelength for the sensor, so that the pinhole diameter is less than that wavelength. The MSPR sensor further includes a light source directed at the sensor bead that is operable to induce the SPR response. Thus, the light source provides light at the resonant wavelength for the sensor, and may be preferably be monochromatic at the desired wavelength. The light may be directed at the coated surface of the bead or at the pinhole, with a detector positioned to receive light transmitted through the MSPR sensor bead.

Due to its small size the MSPR sensors of the present invention can be incorporated into micro-fluidic devices in order to get information about the (bio)chemistry occurring inside the micro-fluidic channel. These devices will allow manufacture of compact, disposable sensors which can rapidly detect and quantify multiple (bio)chemicals, viruses and bacteria, as well as their concentrations, using small sample volumes. Thus, the MSPR sensor of the present invention will have important applications in medical diagnostics and therapeutics (especially the diagnosis and treatment of sepsis), in laboratory instrumentation for monitoring chemical reactions and in detection of biochemical and biological hazards (e.g. bioterrorism or pollution).

In general the MSPR sensor of the present invention can be applied to applications in which interaction with (bio)chemicals changes the refractive index of the bulk media in contact with the surface of the sensor. In the case of a functionalized detector, the present invention can be used in applications in which the chemical interaction causes changes in thickness or compactness of the self-assembled monolayer that covers the surface of the sensor bead and can chemically interact with the analytes or ligands. Some general (not limiting) applications of the MSPR sensor of the present invention include:

1. A method to functionalize the detectors inside microfluidics devices.
2. Applications detecting molecular species interactions inside micro-fluidic channels.
3. Applications detecting small molecular species.
4. Determination of specific binding between molecules.
5. Measurements of affinity constants and dissociation constants of specific molecular pairs, e.g., ligand-receptor pairs, ligand-antibody pairs.
6. Determination of chemical concentrations of analytes inside a micro-fluidic device.
7. Determination of diffusion coefficients of chemicals in restricted geometries.
8. Detection and quantization of molecular species in bodily fluids, such as blood plasma and urine, in real time.
9. Detection and quantization of (bio)chemical or biological hazards in air and water in real time.
10. Detection of molecular species to control release of therapeutic agents in real time, for instance to control disease states.
11. Detection of hazardous waste or industrial chemicals in air or water in real time.
12. Real time detection of viruses in blood plasma and other body fluids.

13. Determination of blood chemistry in human and veterinary applications.
14. Detection of explosives or explosives/firearms residue.
15. Detection of DNA and/or RNA, or detect binding or DNA/RNA with certain proteins on the order of single cells or at most a few cells.
16. Process analysis and/or control for chemical or biochemical industrial processes.

One benefit of the present invention is the elimination of the complicated optics required for conventional planar sensors. For instance, the MSPR sensor of the present invention can use diffuse light from a low-cost light source. The light need not be polarized, filtered or directed. The present invention eliminates the need for fragile, yet bulky, optical alignment components, such as the goniometric mounts in the prior systems.

A further benefit of the MSPR sensor of this invention resides in its capability to be integrated into a small package, or chip. The inventive MSPR sensor allows the light source and the light detector to be positioned very near the sensor bead array, thereby significantly reducing the profile of the present MSPR sensor over prior planar sensors.

It is one object of the invention to provide a micro-sensor that is capable of detecting the presence of target analytes, ligands or molecules in a fluid. A further object is to enhance the sensitivity and speed of detection of the micro-sensor.

Yet another object of the present invention is to provide a sensor that may provide high throughput detection in micro-environments. Other objects and benefits of the invention will become apparent from the following description.

DESCRIPTION OF THE PREFERRED EMBODIMENTS

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
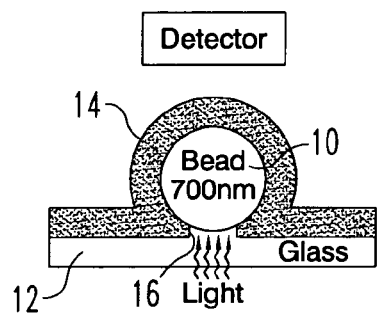
FIG. 2 is an enlarged schematic representation of an SPR sensor in accordance with one embodiment of the present invention.

In accordance with one embodiment of the invention, a resonant microcavity sensor (MSPR) comprises a spherical dielectric microparticle 10 supported on a substrate 12, as depicted in FIG. 2. The microparticle is coated with a layer 14 of SPR-supporting material, such as gold, that is excited through a near-field pinhole 16 defined between the microparticle and the substrate. The light scattered from the coated microparticle exhibits strong spectral resonances associated with the coupling of surface-plasmon modes. These resonances can be used for sensing purposes, like the surface-plasmon resonances used for studies of molecular binding on planar surface-plasmon sensors, but with the advantages of a submicron footprint and the high quality factors of microspherical resonators, yielding a 100-fold improvement over prior sensors that require optical alignment.

These significant improvements over prior planar sensors are accomplished, in part, because the sensor of the present invention relies upon light transmission rather than reflection. It is known that reflected light in nano-contexts yields near-field evanescent-wave light on the far side of the surface of the reflective substrate. The pinhole 16 at the interface between the microparticle 10 and the substrate 12 has a diameter less than the wavelength of the light directed to the surface of the substrate, so only near-field evanescent-wave light will pass through the pinhole. However, the light passing through the pinhole is, by itself, insufficient for a sensor to function. Thus, in accordance with the present invention, the addition of the spherical resonant cavity above the pinhole converts this near-field light to far-field light that can be readily sensed or observed. The symmetrically shaped microparticle over the pinhole allows the transmission of light through the pinhole into the resonant cavity to produce easily observed light transmission above the microparticle. In a specific embodiment, a laser diode provides light at a wavelength of 590 nm, so the pinhole 16 has a diameter less than the wavelength, and more preferably a diameter of less than 300 nm. In certain examples described herein, the pinhole diameter established at the contact between the SPR bead and the glass substrate is in the range of 150-200 nm for a dielectric micro-particle with a diameter of 771 nm. It is contemplated that smaller pinhole diameters will be generated for smaller dielectric micro-particle diameters.

As expressed above, the MSPR sensor of the present invention does not require the complicated optics associated with prior SPR devices that rely upon surface plasmon waves propagating along a flat substrate surface. In particular, the MSPR sensor shown in FIG. 2 does not require a light source on a goniometric mount or collimation and filtering optics for evaluating changes in the SPR angle associated with prior art devices like the device depicted in FIG. 1. Instead, the MSPR sensor of the present invention may be illuminated by light transmitted substantially perpendicular to the substrate 12 into the MSPR sensor beads. Moreover, contrary to the prior art devices of FIG. 1, the light source may be situated on either side of the substrate, as explained in more detail herein.

Furthermore, this freedom from the optical constraints of the prior devices allows the MSPR sensor of the present invention to utilize a wide range of light sources at a wide range of frequencies. For the purposes of the present disclosure, reference to "light" is not limited to visible light wavelengths. Thus, the light source (or more broadly the energy source) may provide light in the ultraviolet, visible and infrared spectral ranges. Although wavelengths outside the UV and IR ranges are not presently known to be used in surface plasmon sensors, the invention does not exclude any later discovered energy wavelengths that observe the plasmon resonance characteristics of the present invention.

Example 1

Fabrication of an MSPR Bead Sensor

The following is a description of one method for laboratory fabrication of the MSPR sensor shown in FIG. 2. It is understood that other fabrication techniques are possible for specific applications. It is further understood that the immediately following description is principally for a sensor adapted for research use, rather than for commercial application, although the same principles may be applied to produce a commercially viable sensor.

Microscope cover glasses No. 1, 30×24 mm, 156 µm thick, are scored with a diamond and broken into four equal pieces. Also, microscope slides, 25 mm×75 mm are scored and broken into two equal pieces. The slides and cover glasses (items 12, 62 and 64, respectively, in FIGS. 2 and 4) are cleaned using a modified version of the well-known RCA cleaning protocol ($H_2O_2$:$H_2O$:$NH_4OH$-2:1:2, warmed to 70° C.) followed by rinsing in Di water and drying with $N_2$. The cleaned cover glasses are placed in a dry atmosphere in a bell jar that can be connected to a mechanical pump in order to create low vacuum inside. Diluted solutions of polystyrene microspheres, about $10^4$ beads/μL with diameters 360 nm, 480 nm and 770 nm, are prepared in advance and 50 μl of each solution is dispensed on each piece of cover glass. Due to the cleaning solution, the surface of the glass turns hydrophilic. After 2-3 hours of exposure to the vacuum in the bell jar (~1 torr) the liquid dries out and the beads remain fixed on the cover glass, forming a random, mono-dispersed layer of beads. The concentration is chosen so the average distance between neighboring beads is sufficiently large (at least 20-50 μm) to avoid optical cross talk. These samples are sputter coated with a 150 nm layer of gold by exposing them for eight minutes to argon plasma.

Figure 3:
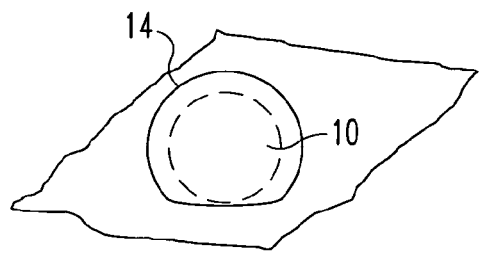
FIG. 3 is an electron-microscopic image of an SPR bead sensor fabricated according to the present invention.

An electron-microscope image of a 771 nm polystyrene bead, sputter coated with 150 nm gold on a glass substrate is shown in FIG. 3. It is understood that the sputter coating is capable of producing the pinhole interface between the bead 10 and the glass substrate 12—in other words, the pinhole is substantially free of the coating material. The light emitted by the MSPR sensors of the present invention when illuminated with white light from underneath the bead sensors is about 100 times more intense than the light transmitted through a flat gold layer of the same thickness.

Example 2

Fabrication of a Micro-fluidics Chip with MSPR Sensors

Figure 4:
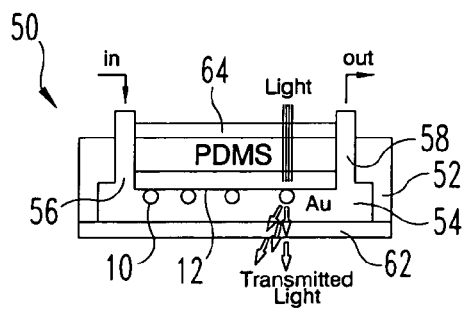
FIG. 4 is a schematic view of a micro-fluidic chip utilizing the SPR sensor according to the present invention.

According to another embodiment of the invention, a process is provided for the fabrication of the sensors of the present invention in a micro-fluidic chip, such as the chip 50 shown in FIG. 4. Variations of the same protocol will allow fabrication of more complex sensors. In this process, the MSPR sensors are mounted within a housing, which in the preferred embodiments is in the form of a micro-chip. The micro-chip format for the MSPR sensor allows the sensor to be readily integrated into micro-systems, such as a micro-fluidics chip described herein.

In accordance with this embodiment, the fluidics chip is made using photolithographic technology and chip replica molding in polydimethylsiloxane (PDMS). The fluidics devices are fabricated using the negative-tone photoresist SU-8 as a master to cast PDMS channel structures. The master substrates are 50 mm×50 mm glass slides. The substrates are cleaned in HCl:HNO3 (3:1), rinsed with de-ionized water, dried with $N_2$, sonicated in methanol and acetone (2:1), and again dried with $N_2$. The master is made with one SU-8 2070 photoresist layer about 100 μm thick. The photoresist is spin coated on the glass substrate at 3000 rpm for 30 sec and ramped at 120 rpm/sec. After pre-baking on a hot plate for 15 minutes at 65° C. and 90 minutes at 95° C., the photoresist is then exposed to UV light of 365 nm wavelength. The UV exposure system is equipped with a high pressure Hg arc lamp filtered to pass 360±45 nm, and the exposure dose is 300 mJ/cm². The exposed photoresist is post-baked on the same hot plate for ten minutes at 65° C. and 30 minutes at 95° C. and cooled to room temperature. The master is then developed for ten minutes, rinsed with 2-propanol, and dried with $N_2$.

The fluidic pattern is transferred to the photoresist through a photomask drawn using AutoCAD2004 LT and printed on a transparency. The fluidic pattern in the illustrated embodiment represents a rectangular fluidic chamber 54 (15 mm×10 mm) having two identical channels, an input channel 56 and an output channel 58 (5 mm wide and 10 mm long). The fluidic chamber depth is limited by the depth-of-field of the 60× immersion oil microscope objective used to analyze the sensors. The fluidic chamber has to accommodate the substrate 12 (156 μm thick in the present example) holding the beads 10 covered with the gold layer 14 shown in FIG. 2. To provide a fluidic chamber having a depth of about 300 μm, the fluidic chamber part of the master is modified by binding a piece of glass substrate 62 identical to that holding the beads. Preferably, the substrates 12 and 62 have substantially the same optical properties and thickness.

The silicon elastomer kit contains a polymer base and curing agent that are mixed in a 10:1 ratio for five minutes. A tape barrier is placed around the mold to hold the elastomer mixture, and the elastomer is poured onto the master. The PDMS in the mold is placed under low vacuum (~1 torr) for one hour to enhance fluidic pattern replication and cured by heating at 120° C. for twenty minutes. The PDMS substrate is then separated from the master, and access holes for fluid connections to the channels are punched through the elastomer with a 16 G needle.

At the bottom of the fluidic chamber of the PDMS chip 50 the substrate 12 holding the beads covered with gold is attached to the ceiling of the fluidic chamber 54 of the PDMS chip 50 with a drop (50 μL) of PDMS. The substrate is placed with the sensors facing away from the PDMS mold and exposed to the inside of the fluidics chamber. The binding is final after ten minutes baking at 90° C.

The fabricated PDMS substrate and a 25 mm×50 mm No. 1 cover glass 62 are then permanently joined after being exposed to air plasma for 40 seconds prior to contact. To increase the rigidity of the chip 50 and to eliminate mechanical perturbations in the flow, a half microscope slide 64 (25 mm×38 mm) is permanently bound on top of the chip using the same air plasma technique. In this example, the depth of the fluidic chamber is estimated to be less then 50 μm in one specific embodiment so that the sensors can be brought into the focus of a 60× oil immersion objective with a working distance of 200 μm.

Example 3

Operation of the Micro-fluidics MSPR Sensor Chip

In one method of using the micro-fluidics chip 50 (FIG. 4), fluid connections from the fluidics chip to fluid reservoirs, such as a syringe or a fluid pump, are made using 1.6 mm OD polypropylene tubing. The flows are controlled by adjusting the height of the reservoir connected to the input channel 56 relative to the height of the reservoirs connected to the output channel 58, or controlled by the fluid pump, so that a stable flow of about 1 μL/s is achieved. After the chip is connected to the reservoirs it is placed on a piezo-driven stage capable of motion in all three directions (3D) that can position the sensor chip in space with a precision of 10 nm. The whole ensemble is placed under an inverted microscope and microscope objectives of 40× and 60× are used to collect and analyze the signal coming from a single sensor.

Figure 5:
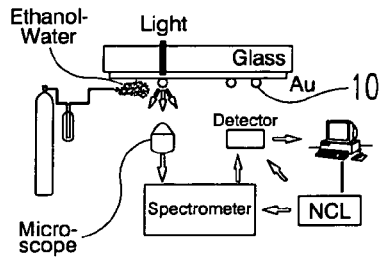
FIG. 5 is a schematic representation of an experimental set-up for evaluating the performance of an SPR sensor according to the present invention.

The functionality and sensitivity of the MSPR sensor 50 may be evaluated using an experimental set-up shown in FIG. 5. In one experiment, the sensitivity of the sensor to vapors is tested. The substrate holding sensors is placed on a 3D-piezo-driven stage that can position the sensor in space with a precision of 10 nm. The whole assembly is placed on the stage of an inverted microscope and microscope objectives of 40× are used to collect and analyze the signal coming from a single sensor. The light coming from the sensor is fed through a parallel port into a monochromator driven by a data acquisition interface unit. Spectra in the visible range from 400 nm to 800 nm may be recorded on a PC with a resolution of 2 nm and 1 sec detector integration time.

Figure 6A:
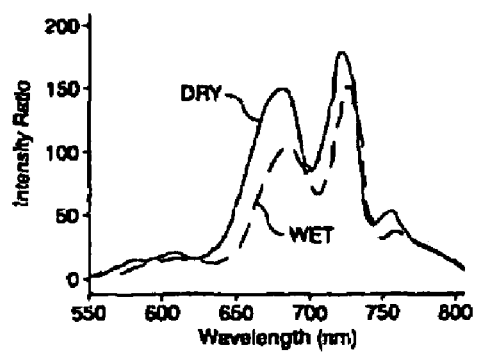
FIGS. 6a and 6b are graphs of the spectral performance of the SPR sensor in the experimental set-up shown in FIG. 5.
Figure 6B:
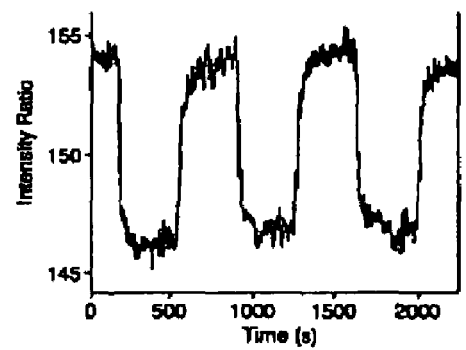

In accordance with one embodiment, the experimental set-up includes a tube connected to a bubbler placed in the proximity of the sensor and $N_2$ is purged through a solution of water: 200 proof ethanol (2:1). The vapors are periodically turned on and off in order to check the sensor's response to the stimulus. Spectra of the light emitted by the dry sensor and the wet sensor are recorded, as shown in FIG. 6a. The peak most sensitive to vapor concentrations is preferably chosen for recording the time-series of the transmitted light, as shown in FIG. 6b. (The abscissa in both graphs corresponds to the ratio of light intensity between the SPR bead and the flat film surrounding the bead). The graph in FIG. 6a shows the spectral shifts in the light transmitted through a 771 nm Au-coated bead due to water (the continuous line corresponding to 50% humidity at ambient atmosphere) and ethanol vapor adsorption (the dotted line corresponding to 75-80% humidity with the vapor access open). The graph in FIG. 6b shows the measured sensor response (wavelength=715 nm) to cyclic humidity changes between 50% and 80%. The arrows represent the instant when the vapor access was opened (down) or closed (up).

Figure 7A:
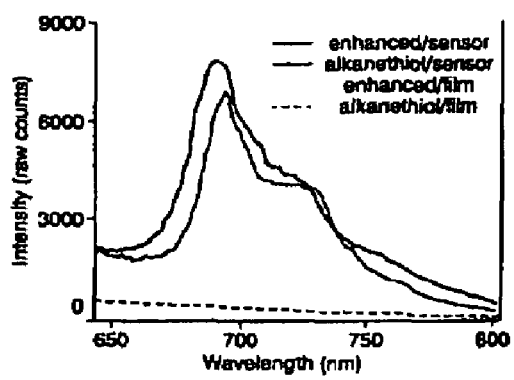
FIGS. 7a and 7b are graphs of the spectral performance of the SPR sensor of the present invention under further experimental conditions.
Figure 7B:
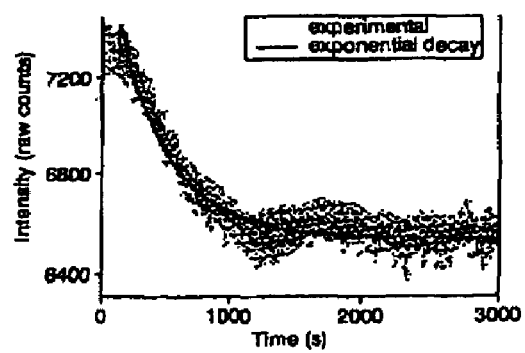

To further verify that the sensor is indeed sensitive to surface modifications, alkanethiol adsorption from ethanol may be employed as a probe. Formation of a single monolayer is known to occur in ~100 minutes at 10 mM concentrations. A comparison of the spectra is provided in FIG. 7a together with the spectral transmission of the flat gold film for the same conditions. The shift of the spectral transmission through a flat film is less than the signal that spherical cavity SPR sensor is expected to record. The spherical cavity sensor of the present invention is thus more sensitive than the flat film sensors of the prior art. The spectral shifts in FIG. 7a persist after the dodecanethiol solution is flushed with pure ethanol, indicating that irreversible adsorption of alkanethiol has occurred. The shifts are thus due to the formation of a monolayer at the gold surface. Upon measurement of adsorption kinetics and fitting with a first order exponential decay (FIG. 7b), a time constant is found for the film formation of 382±7 s at a 100 mM dodecanethiol concentration. Note that while the signal in FIG. 7b corresponds to a single monolayer about 1.5 nm thick, the signal-to-noise ratio is good enough to detect binding of fractions of a monolayer.

Example 4

Alternative MSPR Sensor Configuration

Figure 8:
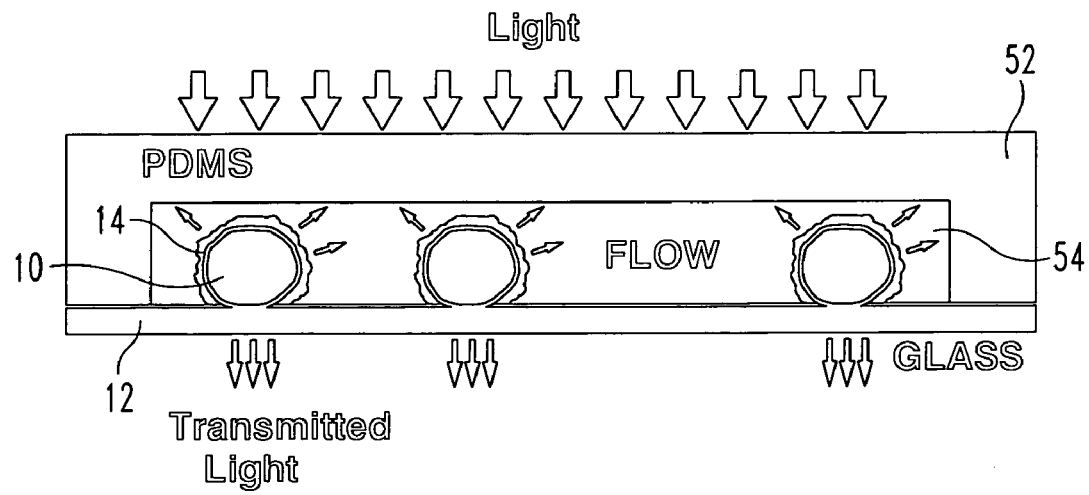
FIG. 8 is a schematic representation of a micro-fluidic SPR sensor according to a further embodiment of the invention.

In Example 1 described above, the sensor responds to excitation through the pinhole 16 (FIG. 2). In an alternative embodiment, the sensor is configured for excitation through the head of the sensor array, as depicted in FIG. 8. In this embodiment, cover glasses No. 1, 24 mm×50 mm and 160 µm thick are used as a substrate. NIST standard polystyrene 780±5 nm diameter beads were prepared in concentrations of about $10^4$ beads/µl in methanol. (Methanol was chosen in this example because it has a very low superficial tension coefficient relative to water and therefore produces a suitable randomly mono-dispersed array of beads). In the example, 70 µl of beads solution was dispensed on each cover glass, providing a bead density of about 5000 beads/mm². After being dried at 1 torr vacuum for an hour, the substrates were sputter coated with a 140-150 nm layer of gold in a masked region of about 10 mm long and 3 mm wide. The substrates were burnt in air plasma for about 3 minutes to ensure that the sensor was clean. Both substrates and PDMS molds were exposed for 45 seconds to air plasma prior to contact.

In this embodiment, the MSPR sensor is positioned within a micro-fluidics structure that permits fluid flow across the random array of beads, as reflected in FIG. 8. The structure may be configured as a T-shape with two micro-fluidics channels that are 50 µm wide and 20 µm deep connected to a common channel 100 µm wide and 20 µm deep. The MSPR sensors are disposed within the common channel. This micro-fluidics structure is molded into the PDMS elastomer and holes are formed in the elastomer to access the two flow channels. The flow channels are connected to two corresponding reservoirs placed at different heights. In this example, flow through the channels is thus accomplished simply by hydrostatic pressure and is on the order of 100 µm/sec. Of course, in other embodiments or commercial versions, fluid flow through the micro-fluidics structure may be accomplished in any manner, such as by a fluid pump.

In this example, a number of MSPR sensors are mounted on the floor of the common channel of the micro-fluidics device, again as shown in FIG. 8. Rather than illuminate the sensors through the pinholes (as in the previous example), the sensors are illuminated through the head of the device—i.e., through the spherical surface of the beads. It was found that the sensor of this example exhibited a resonant response similar to that in the example depicted in FIG. 2, except that the embodiment of FIG. 8 experienced a greater signal-to-noise ratio.

One benefit of the embodiment of FIG. 8 is that enclosure of the micro-fluidics chip is facilitated. In order to enclose the micro-fluidics chips of the present invention, both the glass substrate and the PDMS mold are exposed to air plasma which modifies the chemical structure to bond the two media. Since the MSPR sensors are very small and the spacing between the beads is in the range of 10-100 µm, applying the gold layer, such as by sputter coating, is problematic. In particular, it is difficult to apply the gold layer to the beads only and not to the glass substrate. On the other hand, gold does not bond well to the glass substrate. The embodiment of the present example allows a continuous compact layer of gold to be coated onto the sensor beads and the bottom glass substrate of the sensor. A layer of a material having an affinity for both glass and gold may be added to the glass substrate. In a specific embodiment, the material may be chromium applied at a thickness of about 1-5 nm. Alternatively, the substrate may be subject to a chemical treatment to improve the adherence between the gold and the substrate. The PDMS may then be applied and flows well through the microchannels between the sensors. Post-baking the PDMS molds at 80-100° C. overnight cures the polymer and eliminates any volatiles or loose polymer chains that might infiltrate the gold layer sputtered on the glass substrate.

Example 5

Functionalization of MSPR Sensors

Covalent functionalization on the gold surface of the sensor shown in FIGS. 2 and 8 allows the sensor to be covered with different target analytes, ligands or molecules, particularly biomolecules of high interest. For the purposes of the following disclosure, the term "target" or "targets" shall be used to generically refer to the target analytes, ligands or molecules that are intended to be detected by the sensor. It is understood that these "targets" may include biomolecules, such as proteins, RNS, DNA and enzymes, as well as elements other than biomolecules, such as viruses, bacteria, non-biological chemicals, etc. However, it is understood that these "targets" have the ability to bind with other molecules provided on the MSPR sensors of the present invention and do so in a way that affects the resonant characteristics of the sensors.

Figure 9:
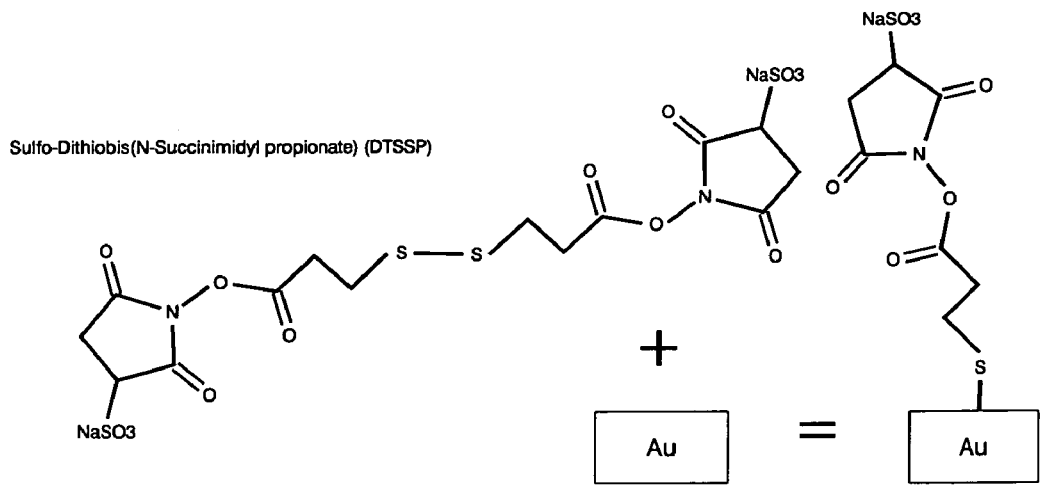
FIG. 9 is a diagram of the sulfo-DSP reaction with the gold layer of the SPR sensors of the present invention for functionalization of the SPR sensors.

In accordance with certain embodiments of the invention, functionalization of the gold layer is accomplished in this example by two different chemistries in the form of a respective monolayer covalently reactive to proteins. The first chemistry is Dithiobis(N-succinimidyl propionate) (DSP, DTSP), also known as Lomant's reagent, which is a homo-bifunctional thiol-cleavable cross-linker that adsorbs onto gold surfaces through the disulfide group. DPS is a highly hydrophobic compound that is soluble in dimethylsulfoxide (DMSO) or dimethylformamide (DMF). A water soluble cross-linker sulfo-DPS (DTSSP) is used to avoid interaction between the DMSO or DMF and the gold surface. The functionalization reaction is illustrated in FIG. 9. In particular, the disulfide bond breaks and reacts with the gold surface.

DTSSP is a semi-stable amine-reactive NHS-ester that is protein reactive. In this example, the reaction is evaluated using two different working buffers-phosphate buffer pH 5.8 and DI water. The reaction kinetics results in a monolayer molecule of 281.52 Da and about 0.6 nm thick at a time constant of 105±8 sec. and a signal-to-noise ration of 5.5

Figure 10A:
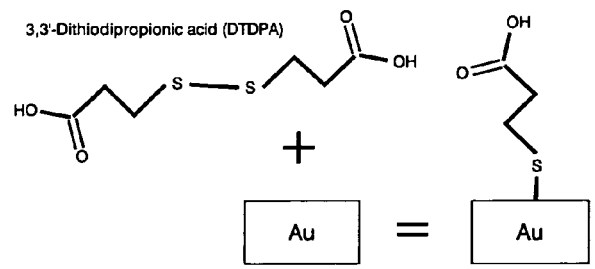
FIGS. 10a and 10b are diagrams of the functionalization reactions using Carbodiimide coupling reagents.
Figure 10B:
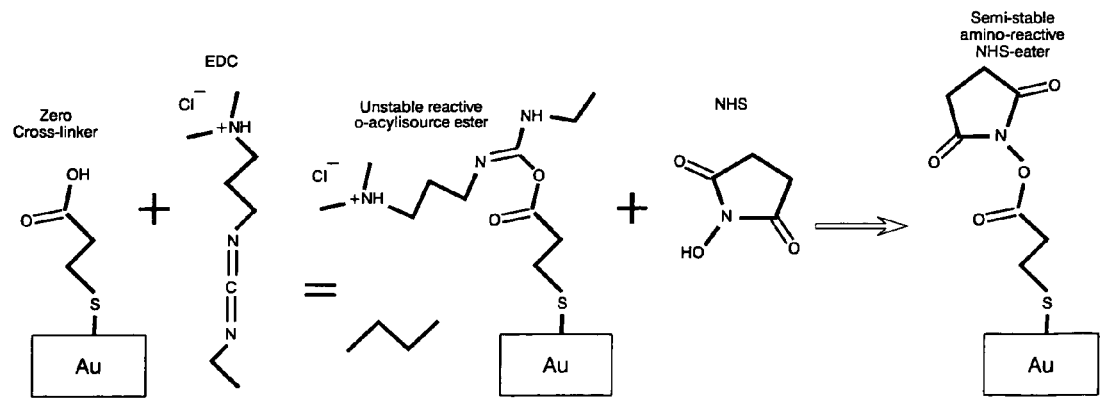

The second chemistry used for the MSPR sensor's functionalization includes Carbodiimide coupling reagents. The reaction involved with this chemistry occurs in three steps. The first step is a reaction of a zero cross-linker with the gold surface, as shown in FIG. 10a. In this first step, the cross-linker is 3,3'-Dithiodipropionic acid (DTDPA) that has a disulfide bond that easily breaks in the presence of gold. This cross-linker ends in a carboxyl group that permits carbodiimide coupling. The DTDPA reaction kinetics yields a molecule of only 104 Da and a 0.5 nm monolayer at the surface of the sensors. A carbodiimide mediator 1-Ethyl-3-(3-dimethylaminopropyl)-carbodiimide (EDC) is employed to readily react with nucleophiles. The EDC solution is prepared in ethanol because the EDC can hydrolyze very quickly. The same solution also contains an amine-reactive ester, such as N-Hydroxysuccinimide ester (NHS). In the complex reaction illustrated in FIG. 10b the EDC and NHS promote a carbodiimide coupling reaction that converts the carboxylic acid into a reactive intermediate that is susceptible to attack by amines. Thus, the final product is amine reactive and ready to bind proteins to the surface of the MSPR sensor.

The reaction kinetics of this second chemistry was found to form a monolayer of 98.1 Da and about 0.5 nm thick on top of the zero cross-linker with an estimated time constant of 28.5±0.9 sec. at a signal-to-noise ratio of 16.2.

Example 6

Protein Binding to a Functionalized SPR Sensor

One significant application of the sensors of the present invention is as a bio-sensor. Thus, a sensor functionalized in the manner described in Example 5 may be used to detect certain protein molecules that are capable of binding to the functionalized chemistries. Two important bio-molecules are glucose oxidase (Gox) and glucose (Glu).

Gox is a very large molecule made of two identical subunits having a total MW of 160,000 Da. Thus, Gox provides a good test to assess the ability of the MSPR sensor and micro-fluidics device to respond to binding of large molecules. Gox is know to bind to gold in a particular orientation and to an EDC/NHS activated gold surface in a different orientation. In this example once the gold surface of the MSPR sensor is activated with the amine-reactive NHS-ester groups, as described above, reaction to proteins is simple but the reaction time constants will depend upon the size of the protein. For a DTSSP functionalized sensor, the reaction time constant was found to be 562±35 sec with a signal to noise ratio of 3.85. This reaction covered the sensor surface with a monolayer of about 10 nm thickness. In this reaction it was determined that the MSPR sensors of the present invention exhibited a sensitivity of 42 zepto-moles/SPR sensor, or expressed as Gox mass covering the sensor a detectability of 6.7 femtograms/MSPR sensor. Variations of this procedure were implemented to monitor the Gox activity under the influence of a flow of $\beta$-D+Glucose 100 mM in PBS 1×, or a flow of Glu 1 mM in PBS 1× (to simulate normal glucose concentration in human blood), or a flow of L-Glucose, or a flow of 2-Deoxy-D-Glucose (2-DxGlu). The device in the present example was able to detect the enzymatic activity of Gox in the presence of $\beta$-D+Glucose 100 mM and 1 mM (except that for the latter case the response was much slower), but no enzymatic activity response was recorded for Gox exposed to L-Glucose or 2-DxGlu.

The above examples demonstrate the efficacy of the MSPR sensor and micro-fluidics features of the present invention in detecting large and small targets, including bio-molecules such as important proteins. In particular, the MSPR sensors of the present invention can be configured to a footprint of less than 1 µm and are still capable of detecting specific binding of zeptomoles of unlabeled targets. In accordance with the present invention, the light source in the optic setup may be a laser diode. In the examples, the selected laser diodes resonated at a wavelength of 590 nm; however, it is contemplated that other small laser diodes may be used at other wavelengths. It is believed that a laser diode resonance at a wavelength of 632.8 nm may help optimize performance of the SPR sensors of the present invention.

It is contemplated that light sources other than the above-described laser diode may be used. For instance, in certain alternative embodiments, a light source may incorporate an optical filter operable to limit the transmitted light to a desired wavelength(s). The optical filter may be tuned at the time of installation of the MSPR sensor to a specific resonant frequency. Alternatively, the optical filter may be positioned at the detector side of the sensor.

The selection of optical detectors can enhance functionality and efficiency of the MSPR sensors of the present invention. In one specific embodiment, the detector may be a low dark current silicon avalanche photodiode (APD) photon counting detectors. Alternatively, for detecting multiple targets in parallel, a CCD camera or other pixel oriented device may be used. The detectors and associated electronics can determine a baseline resonant peak for the MSPR sensors to calibrate the sensor. In use, the detectors may determine whether the resonant peak has shifted (red or blue), which is a direct indication that the target has bound to the resonant surface of the MSPR sensors.

The invention contemplates detectors that are qualitative—i.e., that simply detect the presence of a particular target—or quantitative—i.e., that detect the level or change in level of the target. In the latter case, a quantitative analysis can be particularly valuable to measure the change in analyte concentration over time. For instance, changes in certain toxins in a patient's blood may be monitored, rather than simply discrete instantaneous level, thereby facilitating early diagnosis of a harmful medical condition. The example herein regarding detection of sepsis may benefit from this quantitative approach. Similarly, at home quantitative monitoring of blood sugar levels may be used for earlier detection of diabetic conditions.

In the embodiments described above, the gold layer is sputter coated onto the MSPR beads and the glass substrate. Since adhesion between gold and glass is poor, the manufacturing process may include sputtering a thin layer of chromium onto the glass before adding the gold layer, since chromium binds well to glass and gold binds well to chromium. For high throughput manufacturing, both layers may be applied by a twin head sputter coater to avoid the need to break the vacuum around the substrate.

Figure 11:
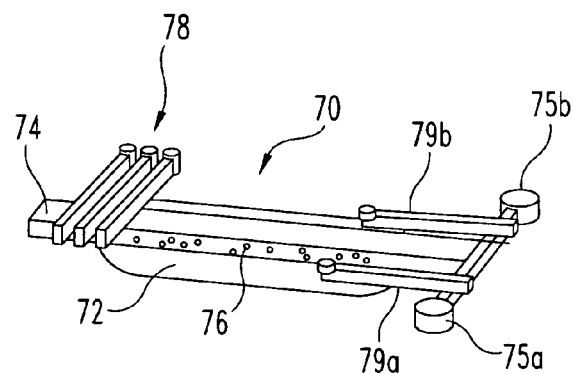
FIG. 11 is a diagram of micro-fluidic components mounted on a micro-fluidic SPR sensor of the present invention.

In the above examples, fluid flow through the micro-fluidics device was accomplished by hydrostatic pressure only. Alternatively, the micro-fluidics sensor chip may incorporate micro-valves and peristaltic pumps to control fluid flow and sample delivery. The use of this micro-fluidics technology will also allow the micro-fluidics sensors of the present invention to process small sample volumes, on the order of 2 μl. Thus, a micro-fluidics MSPR sensor in one embodiment of the invention may be configured as shown in FIG. 11. The sensor 70 includes a MSPR substrate 72 with a T-shaped micro-fluidics structure 74 mounted thereon. The T-shaped structure 74 operates in the manner described above to direct fluid from the channels 75a, 75b of the structure to the common channel 76 over the MSPR sensors. A second level of the micro-sensor 70 includes the fluid control components. In particular, a micro-fluidic pump 78 is provided at the discharge end of the common channel 76. In specific embodiments, the pump may be peristaltic, thermal, or piezo-actuated. Each channel 75a, 75b is provided with a corresponding micro-valve 79a, 79b to control fluid flow through the respective channel into the common channel 76. In a single analyte detection sensor, such as the micro-sensor 70 shown in FIG. 11, one channel 75a and valve 79a controls flow of the sample into the common channel, while the other channel 75b and valve 79b controls flow of the functionalization solution.

It is contemplated that the micro-fluidics components may be electronically controlled to operate in a pre-determined sequence for functionalizing the MSPR sensor array and analyzing a fluid sample. In particular, valve 79a may be closed and valve 79b opened to permit introduction through channel 75b of functionalization solutions, such as the functionalization composition as described above. Once the SPR sensors are functionalized, a buffering solution may be introduced through the channel 75b. The valve 79b may then be closed and valve 79a opened to accept the sample fluid through channel 75a to contact the fully functionalized SPR sensor array. Of course, it is contemplated that the functionalization step may occur remote from the sample analysis—i.e., in the preparation of a pre-packaged biological micro-sensor.

In addition, the pump and micro-valves may be controlled as necessary to ensure sufficient formation of the monolayer of the target on the functionalized MSPR sensor. For instance, in the Gox example above, the formation of a 160,000 Da monolayer about 10 nm thick was detected with a time constant of about 562 seconds. Thus, the flow of test fluid through the micro-fluidics chamber must be adequate to ensure the formation of a significant and detectable monolayer of the target.

Another aspect of the fluidics element of the inventive sensors is dependent upon the nature of the fluid sample being evaluated. In particular, a complex sample requires cleaning and pre-concentration before analysis to ensure accurate detection results. Such complex samples include human blood, which may be evaluated for certain proteins as described in the functionalization examples above, and natural water, such as water from a river being evaluated for the presence of dangerous pathogens. Pre-cleaning and pre-concentrating a biological sample may occur prior to introduction into the MSPR sensor system. For instance, centrifugation may be used to clean a fluid sample, but centrifuge machines are not adapted for a micro-fluidics environment. Large-scale sample testing, such as a drinking water purity monitor, may be amenable to this scale of pre-cleaning and pre-concentrating. However, one feature of the present invention is that is very well suited for micro-fluidics applications in which the entire sensor and associated sample fluidics are present on a single small chip.

Figure 12:
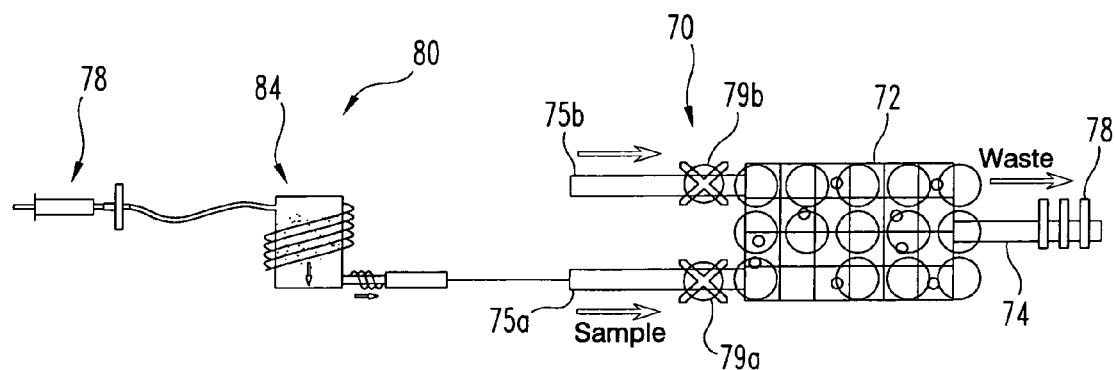
FIG. 12 is a diagram of a micro-fluidic SPR sensor of the present invention with micro-fluidic filtering and pre-concentration modules.

Thus, the present invention contemplates the addition of micro-fluidic filtration and pre-concentration modules that are integrated onto the MSPR sensor chip. Thus, a system 80 shown in FIG. 12 may incorporate a micro-fluidic filter module 82 and a pre-concentration module 84 upstream of the MSPR sensor chip, such as the chip 70 illustrated in FIG. 11. In this embodiment, the upstream modules are connected to the fluid sample channel 75a and valve 79a.

The micro-fluidic filter 82 in a specific embodiment includes a porous membrane sandwiched between opposing PDMS molds. The flow area of the filter depends upon the fluid sample being tested. For instance, a filter area of about 2.5 cm$^2$ is sufficient for low volume filtering, such as up to 1 ml of blood. Larger filter areas may be required for higher volume, or higher flow rate sampling.

In general, filtration removes some of the targets that are desired to be detected. For instance, many proteins will non-specifically bind to filter membranes. Thus, in some cases a pre-concentration module 84 may be interposed between the filter module 82 and the sample channel 75a of the micro-fluidics sensor chip. A variety of pre-concentration approaches may be acceptable, such as electrophoresis, capillary separation, functionalized magnetic bead, isotachophoresis, column separation or photo-activated polycarbonate (PPC) micro-fluidics chips.

Figure 13:
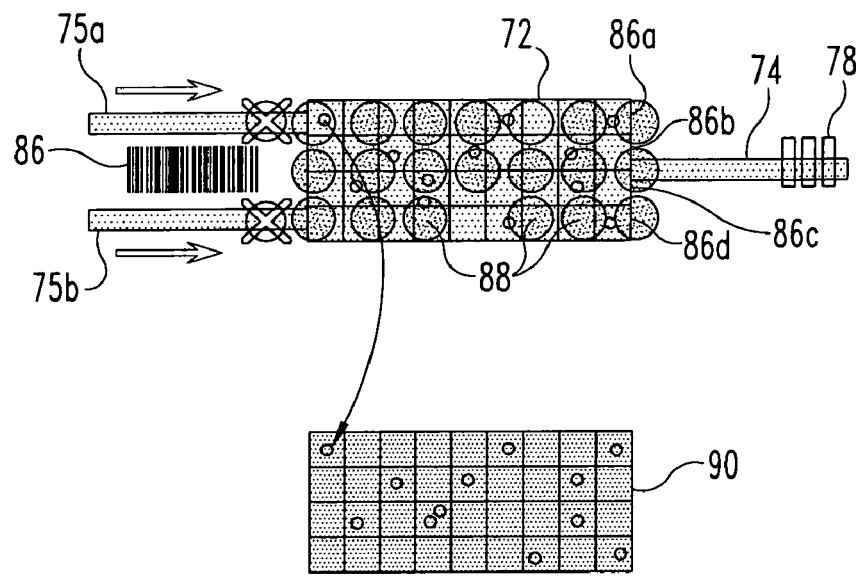
FIG. 13 is a diagram of a micro-fluidic SPR sensor of the present invention with mapped functionalization for detecting multiple molecules, ligands or analytes.

The small size and the accuracy of the MSPR sensor chip of the present invention allows the fabrication of sensors with throughput and massively parallel processing capabilities that greatly exceed the capabilities of current sensors and biosensors. In particular, the MSPR sensors of the present invention can be configured to detect thousands and even millions of targets, all on a single small sensor chip. As shown in FIG. 13 the sensor chip includes a plurality of MSPR beads on a single chip that may be arranged in randomly monodispersed arrays or in regular arrays. The arrays of MSPR sensors may be produced using photolithography and/or holographic optical tweezing, or any other suitable technique for placing microscopically small objects onto a glass substrate. However, one feature of the present invention is that millions of the micro-sized MSPR beads may be completely randomly dispersed on the substrate using currently available technology. As explained below, in spite of this random dispersion of MSPR beads, sensors made according to this embodiment of the invention may be fully functionalized to detect a vast number of targets.

In order to accommodate the need to detect multiple target, current planar SPR sensor technology requires uniformly distributed SPR elements to ensure adequate detection capabilities for multiple targets. The relatively low sensitivity of these current sensors dictates that a sufficient number of SPR elements be associated with predetermined "spots" in which all elements are functionalized to a particular target. However, the ability to accurately place uniformly distributed SPR elements is very limited, generally not exceeding a 100 by 100 grid of elements. This limitation, coupled with the accuracy limitations of the current planar sensors, ultimately limits the number of discrete targets that can be detected to less than about 1000, which ultimately severely limits the range of applications for these sensors. For instance, gene therapy and human genome mapping projects yield millions of targets for detection. Using the current planar technology, hundreds of the bulky sensors would be necessary for projects of this nature.

On the other hand, the capability exists to randomly disperse the micro-beads utilized in the sensor of the present invention. However, until the present invention, there has been no way to capitalize on this ability to populate a sensor substrate with millions of SPR elements, each capable of being functionalized individually or in groups of spots. In accordance with the present invention, one method of achieving this discrete functionalization is to operate on groups of sensors by flowing reagents over specific bands of the sensor chip using micro-fluidics. In other words, as seen in FIG. 13 the chip 72 may be divided into multiple bands, such as the four lengthwise bands 86a-d. A micro-fluidics system may then flow a specific reagent along each band to commonly functionalize each MSPR sensor along the band. This approach limits the degree of functionalization to the number of bands on the chip over which the various reagents may accurately flow. In one specific embodiment, the MSPR chip may be divided into about twenty bands, each with different functionalization so that a like number of targets may be earmarked for detection.

In another approach, individual MSPR sensors may be precisely selected for specific functionalization. One manner of achieving this individual functionalization may be by use of a photo-activation bound cross-linker, such as photo-biotin. However, this method is inherently slow since only a few SPR sensors maybe functionalized at a time. Another more versatile approach is to use a micro-spotter for making micro-arrays of SPR bead sensors, in a manner similar to prior ink jet printers. Some micro-spotter printers are capable of placing ink drops to a resolution of 600×600 dpi, with dot sizes in the range of 30 μm at 45 μm spacing and a volume of only 10 pl. Even more accurate ink jet printers are capable of resolutions of 4800×4800 dpi with each ink dot having a diameter of only 5 μm. This printing technique may be adapted to functionalize selected MSPR sensors or groups of sensors, resulting in functionalized spots, such as the spots 88 shown in FIG. 13. Each spot may pertain to a different target.

In yet another approach, discrete multiple target functionalization may be achieved using a multi-pin spotter. This multi-pin spotter may precisely apply the cross-linker or reagent directly to and only on the MSPR beads. The specifically functionalized beads may be in clusters or randomly dispersed throughout the entire field of MSPR beads.

Figure 14:
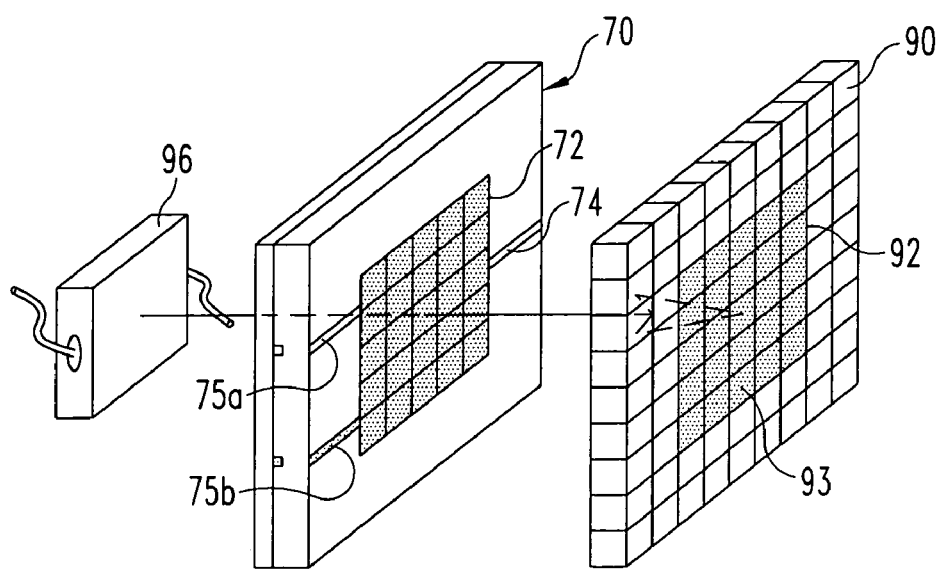
FIG. 14 is a diagram of the components of a micro-fluidics SPR sensor system in accordance with the present invention.

In a further approach to functionalization that is well suited to massively parallel processing, the MSPR beads may be functionalized using a mask. The mask limits the application of the cross-linker or reagent to the MSPR beads disposed within spots 88 on the substrate. It is contemplated that the functionalized spots will encompass random numbers of the randomly dispersed MSPR beads on the array over an area that is significantly larger than the beads themselves. Thus, in a specific embodiment, the functionalized spots may occupy an area about 30 μm in diameter, whereas the MSPR beads have a diameter of about 770 nm. A micro-spotter capable of dispensing reagents in quantities as low as 10 pl may be used to functionalize the beads in each spot. The sensor chip may include a bar code 86 or some other readable signature identifying the various functionalizations as well as spots corresponding to each functionalization. As described below, the bar code 86 may also contain calibration information corresponding to the responsive signals generated by the detector 90 (FIG. 14).

With the sensor construction as thus far described, a plurality of randomly dispersed MSPR beads populate the substrate, with collections of beads commonly functionalized to form spots 88. In the specific example shown in FIG. 13, eighteen such spots are depicted; however, it is contemplated that hundreds, thousands and even millions of such spots may be defined on a given sensor chip. An operational sensor chip requires a light source and some form of detector to sense the resonant response at each spot. Thus, in accordance with one embodiment of the invention, a stack forming the micro-sensor may appear as shown in FIG. 14 with the MSPR sensor chip 72 sandwiched between a detector 90, which may be a CCD array, and a light source 96, which may be an LED. It is understood that various optical conditioning elements may be integrated with the light source and/or detector, such as an optical filter to improve signal/noise ratio. The optical conditioning element may also include a wavelength filter or different discrete wavelength filters corresponding to specific spots 88 or individual MSPR beads.

In accordance with one feature, the detector or CCD array may be mapped into a grid 92, with each pixel 93 of grid containing a CCD capable of sensing light transmission through the MSPR sensor chip 72 and configured to generate a signal indicative of that light transmission for subsequent processing. This mapped grid 92 overlays the sensor chip, as shown in FIG. 14, or alternatively the spots 88 may be regarded as projected onto the mapped grid, as illustrated in FIG. 13. Optimally, the detector grid is fine enough so that each spot 88 may be projected onto multiple pixels 93 of the grid. It is expected that each pixel may overlay several MSPR beads, although the number of beads corresponding to each pixel will vary due to the random distribution of the beads on the substrate.

Calibration of the detector proceeds first by identifying an optimum pixel or pixels reading transmission data from each spot 88. Thus, in a specific example, a particular spot may fully encompass four pixels 93 and partially encompass five additional pixels. The MSPR chip is illuminated by the light source 96 and the measured intensity at each of the pixels corresponding to the spot is evaluated. The pixel registering the greatest response is selected as the pixel corresponding to the specific spot, which in turn corresponds to a specific functionalization. That selected pixel will likely map onto the largest number of MSPR beads relative to the other pixels, hence its greater response relative to the other pixels. The output from the CCD within this selected pixel may then be calibrated in relation to the intensity and/or wavelength of the light source 96. This same process is repeated for all of the other functionalized spots 88. Thus, in the specific example, for the eighteen functionalized spots (FIG. 13), eighteen pixels 93 on the mapped grid 92 of the detector 90 may be identified so that the calibrated output of each pixel will be evaluated. This calibrated output may be written onto an on-board memory or transmitted to a peripheral memory device and/or processor. A calibration table with the calibration data for each of the mapped pixels may be maintained in a memory and accessed by the peripheral processor. The bar code 86 may thus provide an identifier for extracting the proper calibration table from multiple tables stored in memory. The calibration table may identify which pixels to read from the detector and how to interpret the output signal from each pixel. The peripheral device applying the calibration data may be configured to obtain the necessary data from a global database, such as through an Internet link.

It is contemplated that additional pixels may also be associated with a particular spot, with appropriate modifications to the calibration of the corresponding output responses. It should be appreciated that in some cases the output response for a given pixel may result from light transmission through only one MSPR bead present within a given spot and aligned with a given pixel, while for another pixel the light transmission may be measured through several MSPR beads. The random distribution of beads means that the number of MSPR beads used to generate an output signal corresponding to each functionalized spot is also random. However, the calibration step described above can ensure that the targets can be quickly and accurately detected. The high sensitivity of each MSPR bead in the MSPR sensor of the present invention means that even a single MSPR bead may be sufficient for a particular functionalized spot and detector array pixel.

It can be appreciated that the device illustrated in FIG. 14 may open realms of target detection unavailable with prior sensor devices. As explained above, a single MSPR sensor chip may be functionalized to thousands of targets in a small package. The small size of the sensors of the present invention allows the formation of massively parallel arrays of sensors for DNA, RNA and protein detection. The use of micro-fluidics with the sensor chip allows for a continuous flow of test fluid across the sensor chip 70. This micro-fluidics feature facilitates the massively parallel sensor arrays and provides an avenue for real-time accurate sensing of chemical and biochemical conditions.

A particularly beneficial usage is in real-time detection of targets in the blood stream. One important application of the multi-channel embodiments of the present invention is in the detection of sepsis. Sepsis is a major source of mortality in post-surgery recovery and in trauma victims. Treatment of sepsis is largely limited to antibiotics and palliative measures to support heart, lung and kidney function. According to data collected in 2001, sepsis syndrome affects an estimated 751,000 patients in the United States each year, of whom 383,000 (51.1%) received intensive care. Mortality has been estimated at 215,000 deaths nationwide, increasing with age from 10% in children to 38.4% in those 85 years and older. The cost per case averages about $22,000, which means almost $17 billion annually. Early detection of sepsis and rapid intervention (within two to four hours of onset) greatly reduces mortality and debilitation in survivors. However, no current method exists to monitor patients for the onset of sepsis. In many cases the medication produced for sepsis treatment failed due to the lack of instrumentation capable to continuously monitor cytokines levels in patients' blood.

Sepsis syndrome is the body's systemic inflammatory response to infectious stimuli. Endotoxins—such as lipopolysaccharide (LPS) from Gram-negative bacteria, peptidoglycans and flagellan from Gram-negative and Gram-positive bacteria, lipotechoic acid from Gram-positive bacteria, mannan from fungi, and other antigens from infectious agents—stimulate macrophages and monocytes to release tumor necrosis factor alpha (TNF-$\alpha$), followed by a cascade of cytokine release. During the first period of sepsis (especially the first eight hours), excessive inflammatory response can cause massive organ damage, especially to kidneys and heart, but also reaching the liver, lungs and brain, requiring artificial support of blood pressure and ventilation. This organ damage often causes debility or mortality months or years after the acute phase of sepsis.

The release of pro-inflammatory mediators was originally thought to be largely uncontrolled. However, subsequent investigations have demonstrated that TNF-$\alpha$ also stimulates leukocytes to release anti-inflammatory cytokines, including IL-10, IL-1 and transforming growth factor-beta (TGF-$\beta$), which inhibit the synthesis of pro-inflammatory cytokines and exert direct anti-inflammatory effects on monocytes, macrophages, and endothelial cells. This compensatory anti-inflammatory response syndrome (CARS) is intended to localize what would otherwise be an uncontrolled pro-inflammatory response to the infection throughout the body. Unfortunately, the anti-inflammatory response often surpasses the pro-inflammatory response in the later phases of sepsis, resulting in immunoparalysis—i.e., the inability to mount an effective immune response to additional infectious insults.

Figure 15:
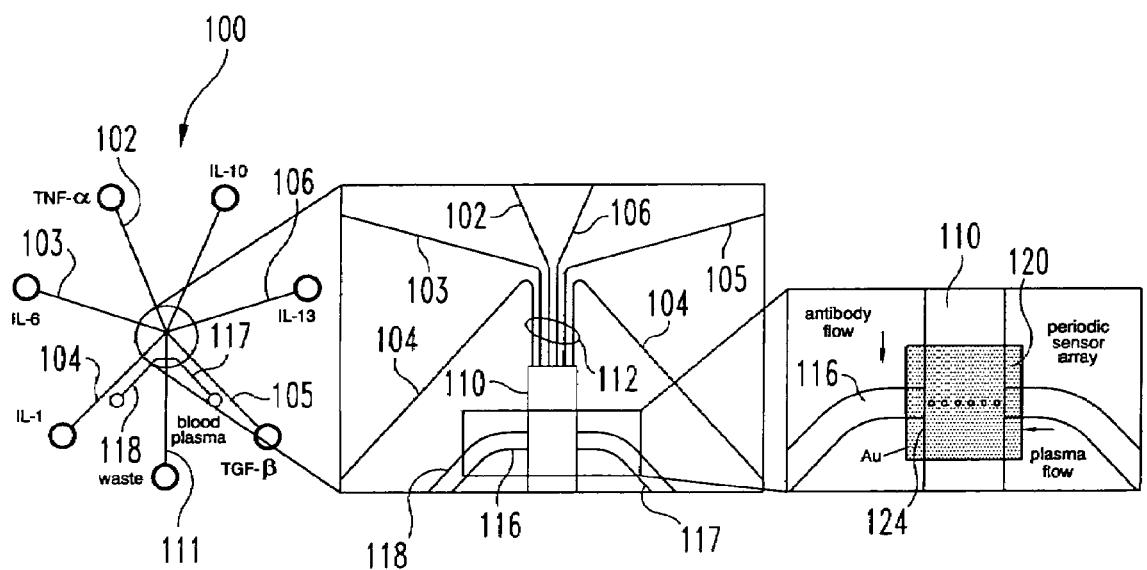
FIG. 15 is a schematic representation of a sensor according to the present invention that is capable of simultaneously evaluating multiple chemicals.

Thus, a minimally-invasive device, which could be attached to all postoperative and post-trauma patients which could monitor the onset and progress of sepsis, allowing for much earlier and more directed intervention, and ultimately reducing both mortality and debility in survivors. In accordance with a particular embodiment, a micro-fluidics device 100, shown in FIG. 15, is provided that can be used to simultaneously analyze a set of six chemicals that play an important role in sepsis. (However, the micro-fluidic structure can be modified to accommodate the analysis of more or fewer chemicals at the same time, or may be modified for different driven flows, flow velocities or analysis set-ups). One manner of diagnosis of the onset of sepsis and its progress involves monitoring the chemicals, TNF-$\alpha$, IL-1, IL-6, IL-10, IL-13 and TGF-$\beta$, at the same time and in real time. Thus, as shown in FIG. 15, the micro-fluidics sensor 100 includes a set of six channels 102-107 (each 50 µm wide, 100 µm apart and 11 mm long in a specific embodiment) that come together into a micro-fluidic chamber 110 (2 mm long and 600 µm wide), with each channel corresponding to a particular monitored chemical. The spacing is chosen so that diffusion of molecules of about 20 kDa will not interfere with molecules in the neighboring channels. These six channels are used to functionalize the sensor array 120 with specific anti-bodies for the above-mentioned chemicals. The flow of different antibodies through the micro-fluidic chamber will create a series of six parallel antibody stripes 112, functionalizing the chip. The chip 100 in this specific embodiment is designed for a flow of the antibody at a minimum 400 µm/s. This treatment and specific calibration can be done prior to usage of this chip to evaluate a sample.

A transverse channel 116 of 200 µm wide intersects the micro-fluidic chamber 110. This channel is wider to permit more viscous and faster coagulating fluids, like blood plasma, to pass though. The region of intersection covers an area of 200 µm×600 µm. The transverse channel 116 includes an inlet 117 through which the blood is introduced, and a waste outlet 118. Similarly, the micro-fluidic chamber 110 includes a waste outlet 111.

This sensor array 120 is preferably oriented at the intersection of the chamber 110 with the transverse channel 116 and preferably aligned with the channel. In one specific embodiment, the sensor 120 may include a linear array of six SPR bead sensors 124 or sensor spots, with each individual sensor or sensor spot corresponding to a particular functionalization and aligned with the corresponding antibody strip 112.

The micro-fluidic device 100 depicted in FIG. 14 may be fabricated using a poly-dimethylsiloxane (PDMS) substrate and a cover glass in the manner set forth below. The devices are fabricated using negative-tone photoresist SU-8 as a master to cast PDMS channel structures. The master substrates are 50 mm×50 mm glass slides. The substrates are cleaned in HCl:HNO$_3$ (3:1), rinsed with nanopure water, dried with nitrogen, sonicated in methanol and acetone (1:1), and dried with nitrogen again. The master is created with two SU-8 photoresist layers. A first under-layer (an 18-20 µm thick layer of SU-8 2010) is used to promote adhesion of the channel structure to the substrate and a second thicker layer (60-80 µm thick layer of SU-8 2070) of photoresist is used to create the channel structure. Both layers are processed identically except that the first layer is exposed without a photomask. The photoresist is spin coated on the substrate at 1000 rpm for 30 seconds and ramped at 40 rpm/second. After prebaking on a hot plate for one minute at 65° C. and two minutes at 95° C., the photoresist is then exposed to UV light. The proposed channel design is transferred to the photoresist through a photomask drawn using AutoCAD 2004 LT and printed on a transparency using a high resolution laser printer at 8000 dpi. The UV exposure system is equipped with a high-pressure Hg arc lamp filtered to pass 360±23 nm, and the exposure dose is 300 mJ/cm$_2$. The exposed photoresist is postbaked on the same hot plate for one minute at 65° C. and three minutes at 95° C. The master is then developed for five minutes, rinsed with 2-propanol, and dried with nitrogen.

The silicone elastomer kit contains a polymer base and curing agent that are mixed in a 10:1 ratio for five minutes. A tape barrier is placed around the mold to hold the elastomer mixture, and the elastomer is poured onto the master. The PDMS on the mold is placed under low vacuum (~1 torr) for one hour to enhance channel replication and cured by heating at 120° C. for twenty minutes. The PDMS substrate is then separated from the master, and access holes for fluid connections to the channels are punched through the elastomer with a 16 G needle.

At the bottom of the PDMS mold, across the micro-fluidic chamber 110 at the intersection with transversal channel 116, the linear array of MSPR beads 120 may be produced using photolithography and/or holographic optical tweezing, or any other suitable technique for placing microscopically small objects onto a glass substrate like using a micromanipulator and a laser tweezers system. The micromanipulator is loaded with a solution of $10^3$-$10^2$ beads/µL, precision-size-standard beads. This concentration is chosen so that the MSPR beads of the array 120 are dispensed having a spacing of about 50-100 µm. An optical laser tweezers can be used to hold the bead in place until the liquid dries and the next bead will be dispensed with the micromanipulator and held with the tweezers until the liquid dries and so on and so forth. Once the beads 124 are placed, the PDMS substrate is sputter coated through a window of 1 mm×1 mm placed above the intersection. The beads are covered with 150 nm of gold. The PDMS substrate and glass cover glass are then permanently joined after being exposed to air plasma for 40 seconds prior to contacting.

In one embodiment, a sepsis detector device may include a catheterization tube connected intravenously to the patient and to a pumping system to periodically draw a small volume of blood into the sensor device 100. The blood passes through a disposable filter to extract the plasma and the plasma is supplied to the disposable sensor 100 through a channel 116. The output from the sensor provides a reading of the cytokine concentrations in the plasma. The waste blood passes through channel 118 to be collected in a disposable biohazard-labeled discard tube. The small size of the MSPR sensor and sensor chip of the present invention allows the sensor device 100 and catheterization tube to be in place as long as the patient is under medical care. Control of the peristaltic pump to draw blood into the sensor chip may be electronically controlled to occur at pre-determined intervals or in response to some other medical condition sensor. The detector of the sensor may be coupled to the same controller to generate an alarm if the particular agents are detected.

Elevated levels of IL-10, IL-13 and TGF-β indicate incipient sepsis, while elevated levels of IL-10, IL-13 and TGF-β indicate immunoparalysis. If the sensing time for each of the sensors is too large, a single channel may not be able to detect the cytokine levels in real time. In that case an array of channel detectors may be fabricated on a single disposable chip and the blood supply switched between channels at five minute intervals. A controllable microvalve may be used to alternately supply blood and clean sterile medium to the sensors to reset them for the next measurement.

Classes of agonist and antagonist drugs have been developed to control the various cytokines involved in sepsis. However, none of these drugs are widely used because physicians have no way to monitor their effects, which vary greatly from patient to patient and over time. The result is that the current treatment of choice includes inflammatory suppressors and enhancers that are given in either insufficient or excessive doses, both of which may be lethal to the patient. The MSPR sensors of the present invention would allow physicians to supply a tailored cocktail of agonists and antagonists which would suppress immune response early in infection and enhance it in late infection, while maintaining the cytokines at optimal levels at all times.

The same principles for detecting sepsis conditions may be applied to the interactive detection of other medical conditions, as well as an interface to collateral therapeutic devices. With appropriate functionalization, a single or multiple-sensor device may be used to monitor patient status during extended treatments. For instance, a MSPR sensor chip and micro-fluidics system in accordance with the embodiments described herein may be incorporated into a dialysis system, or other device that continuously draws blood or other fluids from a patient for treatment. The MSPR sensor chip may be integrated into a continuous blood monitoring system to detect targets in real-time that are indicative of oncoming problems, such as heart attack, stroke, kidney failure and the like.

A second embodiment of the multiple sensor array devices may be provided that comprises of a set of syringe tubes containing cytokine regulatory drugs and controlled by the output of the cytokine detector prescribed above. This device would ultimately supply a controlled dosage of multiple cytokine regulators to the patent via an intravenous (IV) drip, continuously changing the supply of agonists and antagonists to keep the patient's cytokines at optimum levels. In the above blood monitoring example, the real-time detection of targets indicative of the onset of a heart attack, for instance, may be used to provide immediate real-time dosing in response to the onset of that condition.

This same interventional treatment may be employed to stave off sepsis when detected as described above. In this instance, certain anti-sepsis treatments rely upon the action of a particular protein to inhibit the creation of certain target molecules. However, the treatment itself may be immune-suppressant, so the treatment must be carefully administered. Real-time detection of target levels by the MSPR and micro-fluidic sensors of the present invention allow prompt and accurate administration of the anti-sepsis treatment. A similar approach may be implemented to reduce the toxicity of chemo-therapy or HIV treatments, or for other treatments that create target blood-borne markers indicative of the onset or presence of unwanted side effects The disposable MSPR sensor devices described above are suitable for many other applications. For instance, the present invention may be adapted for public and private drinking water testing. The MSPR sensors may be functionalized to detect various organic and inorganic contaminants, toxins, cellular organisms and viruses. The sensors may be positioned within the water supply to continuously monitor the water flow for the selected targets. Since the devices of the present invention rely upon light detection devices, such as the CCD array 90 described above, an electrical signal is generated that may be evaluated and used to initiate a predetermined response, such as a sensible alert.

Devices based on these sensors can be developed for detection of biohazards, noxious chemicals, neurotoxins, explosives, or HIV or other viruses or bacteria in blood, plasma or other body fluids. The present invention allows the sensors to be small enough to be portable and easily disposable. In the illustrated embodiments, the sensor chip fits within a 50 mm×50 mm area. Specific apparatus can be adapted for airport or homeland security use or for use in water treatment plants or factories. Depending on the use, automated systems for connecting to the input reservoirs of the chip can be included and additional chemicals can be analyzed at the same time and on the same chip.

The MSPR sensors and micro-fluidics of the present invention may also be adapted to monitor chemical reactions or bioreactions. The micro-chips of the present invention may be integrated into fluid flow lines or directly within chemical reactors or bioreactors to detect certain target products of the reactions or to detect the chemical conditions within the reactors that may impact the reaction. The MSPR sensors may be used to optimize the reaction conditions or determine when the reaction is complete. This specific embodiment may have beneficial application as part of process control for drug or chemical fabrication, especially to control the purity of the resultant product.

Micro-fluidics devices endowed with the sub-micron cavity surface-plasmon biosensors of the present invention overcome several deficiencies in prior sensing techniques and devices. Combining the properties of the micro-fluidics devices with the sensitivity of the MSPR bead sensor extends the boundaries of the lab-on-a-chip ideal by increasing detection abilities inside the micro-fluidics chip or confined spaces.

Current devices monitor molecular interactions and molecular kinetics using planar SPR or the older ELIZA kits. In order to excite surface plasmons on a planar metal surface certain restrictions must be obeyed. In particular, the source of light must be p-polarized and a precise critical angle of incidence must be obtained in order to produce a maximum coupling between incoming photons and surface polaritons. The sensor of the present invention combines the sensitivity of surface plasmons with the resonant properties of a spherical sensor. Besides a boost in sensitivity, the invention relaxes constraints on the geometry and polarization of the light source. Moreover, the sensor has a footprint of a square micron or less, which makes it well-suited for miniaturization (having an active area of about one thousand times smaller than the present state-of-the-art SPR planar sensors) while increasing sensitivity and improving the ability to integrate into micro-fluidic structures. Furthermore, the MSPR sensors of the present invention work in transmission compared with the prior SPR sensors that work in reflection. Due to this difference, a sensing micro-fluidics chip incorporating the MSPR sensor of this invention can be placed very close between the light source and the sensing window of the detector, resulting in a very compact, robust and inexpensive hand-held device.

Micro-fluidics devices are currently the most sophisticated technology for dealing with small quantities of analyte (ranging from picoliters to microliters), and for very precise control of flows and gradients. They are appropriate for multiple replica molding and new configurations of channels and set ups can be produced at very low cost, making them suitable for single-use devices. This property makes them convenient in many areas of research, especially for medical applications. They are suitable for massively parallel processing of chemicals, which can save a huge amount of time, especially in analyzing very complex samples, for example, but not limited to, blood plasma, body fluids, toxic waste, foods, etc. The only time constraint is the reaction time between the specific molecular species in the sample and the receptors bound to the surface of the functionalized MSPR detector.

The MSPR sensor of the present invention takes advantage of these properties of micro-fluidics devices. It has better sensitivity than prior devices due to the coupling of the surface-plasmon with the geometry of the sensor. While current SPR sensors can only detect large molecules, the SPR sensors of the present invention can detect large and small molecules with good sensitivity. The smallness of the sensors allows control, detection and analysis to be achieved on a single chip and to take advantage of the ability of micro-fluidics devices to conduct multiple parallel analyses, which can shorten the analysis time. Moreover, these devices can be disposable and can be produced cheaply.

In the illustrated embodiments, the microspheres are coated with gold. It is contemplated that the spheres may be coated with other metals, such as silver, copper, or gold alloys. However, current experimentation suggests that spectral resonances in the transmitted light occur only for gold-coated spheres or beads, which is believed to be due to the surface plasmon coupling. The film thickness of the gold coating may be adjusted depending upon the application of the particular MSPR sensor. However, it has been found that increasing film thickness causes blue-shifting of the observed resonances, at least for the symmetric (low frequency) mode. Conversely, it has also been found that the frequency for the high frequency anti-symmetric mode is red-shifted with increases in film thickness. Moreover, the spherical geometry implemented in the present invention preferentially excites the symmetric SP modes, thereby minimizing red-shift effects. Experimentation further suggests that some peaks, such as the peak at 623 nm for a 770 nm bead coated with a 150 nm gold layer, exhibits much less sensitivity to the metal film thickness than other peaks.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

In the illustrated embodiments, the micro-particles forming the MSPR sensor are spherical in shape to form a spherical resonant cavity. However, other symmetric geometric shapes may be utilized for the bead shape. For example, the bead may have an elliptical shape or be multi-faceted like a dodecahedron, provided that the shape can sustain periodic boundary conditions for the stationary plasmon wave to travel across the surface of the bead.

The various materials and dimensions set forth for the illustrated examples may also be modified while still maintaining the functionality achieved by the MSPR sensor and micro-fluidics systems of the present invention. Modifications to the materials and dimensions of the MSPR sensor must still fulfill the primary object of the MSPR sensors of the present invention, namely to detect targets Moreover, the modifications must not interfere with the shape or geometric resonant characteristics that are used to enhance the SPR resonance features of the micro-cavity sensor. The detection capability of the MSPR sensors of the invention relies upon binding the target to a coupling reagent layer that it itself bound to the SPR-supporting coating, and ultimately upon the change in optical response.

It is believed that for most targets and coupling reagents the wavelength of the applied light is not critical. On the other hand, the SPR-supporting layer is, by definition, wavelength dependent since the surface plasmon resonance occurs in that layer. Thus, it is believed that modifications to the materials and dimensions of the MSPR sensor are centered on the selection of the SPR-supporting layer material and its characteristic wavelength. In the illustrated embodiments, that material is gold which has a wavelength of 510 nm. In accordance with certain aspect of the invention, this wavelength determines the diameter of the micro-particles or beads 10 and the pinhole 16. The bead diameter is also a function of the refractive index of the dielectric material.

In alternative configurations, the SPR-supporting coating material may be silver, copper, or other non-gold SPR-supporting material, with appropriate changes in coating thickness. Since silver and copper each have a different SPR characteristic wavelength, the selection of either metal as the material for coating 14 will result in a change in diameter for the micro-particle 10 and the pinhole 16. In accordance with certain embodiments of the invention, the micro-particle diameter would be sized to about the characteristic wavelength of the silver or copper coating, while the pinhole diameter would be fixed at less than that wavelength. Similarly, the coating thickness may be modified with a commensurate change in the micro-particle and pinhole diameters.

To the extent that the MSPR sensor dictates the characteristic wavelength, the light source and transmitted light detector (such as the source 96 and detector 90 in FIG. 14) may be selected accordingly. In certain embodiments, white light may be acceptable, while in other embodiments it may be desirable to select a monochromatic light source centered at the characteristic wavelength of the MSPR sensor. Preferably the light detector is calibrated to the characteristic wavelength.

With respect to material selection for the MSPR sensors and micro-fluidics chips of the present invention, the materials in the above examples and embodiments are illustrative. While the MSPR beads are described as formed of polystyrene, other light transmissive materials may be used, such as glass or aluminum oxide. The selected material is most preferably dielectric and has an index of refraction similar to polystyrene. Of course, as indicated above the index of refraction of the bead material affects the optical response and resonant mode of the MSPR, along with the SPR-supporting coating.

Likewise, the material forming the housing or chip around the MSPR beads and substrate may be different from the PDMS material identified in the illustrated examples and embodiments. Preferably, the material is substantially light transparent and exerts only a minimal influence on the optical and resonance characteristics of the MSPR sensor.

With respect to applications or uses of the MSPR sensors and micro-fluidic sensors of the present invention, the foregoing examples and embodiments are not intended to be limiting. It should be appreciated that the present invention permits the rapid and accurate detection of a wide range of targets, whether in small sample volumes or in continuous flow systems. The present invention also permits simultaneous detection of hundred, thousands and even millions of targets in a single micro-sensor or in a massively parallel array of sensors. Thus, even as the present invention may greatly enhance current detection techniques, it will likely lead to new techniques and analyses not yet contemplated.

What is claimed is:

1. A sensor for detecting the presence of a target analyte, ligand or molecule in a test fluid, comprising:
    a light transmissive substrate;
    a surface plasmon resonant (SPR) element mounted on a surface of said substrate;
    an exposed surface of said SPR element having a surface coating of a material capable of binding with the target to be detected;
    a light source arranged to direct light into said SPR element; and
    a detector arranged relative to said SPR element to detect light transmitted therethrough,
    wherein said SPR element includes a light transmissive bead formed in a geometric shape that can sustain periodic boundary conditions for a stationary plasmon resonance wave to travel across the outer surface thereof and
    wherein a pinhole is defined at the interface between said SPR element and the substrate.

2. The sensor of claim 1, wherein said light source is arranged to direct light through said pinhole into said SPR element.

3. The sensor of claim 1, wherein said light source is arranged to direct light into said SPR element opposite said pinhole.

4. The sensor of claim 1, wherein said SPR element and said substrate are coated with a layer of an SPR-supporting material, said layer defining said pinhole at the interface between said SPR element and said substrate.

5. The sensor of claim 1, wherein:
    the light from said light source is provided at a pre-determined wavelength; and
    said pinhole has a diameter that is less than the pre-determined wavelength.

6. The sensor of claim 5, wherein the pre-determined wavelength of the light from the light source is a function of the geometrical shape resonance characteristics of said SPR element.

7. The sensor of claim 6, wherein the pre-determined wavelength of the light from the light source is a function of the maximum dimension of said SPR element at said exposed surface.

8. The sensor of claim 7, wherein:
    said SPR element includes a coating on said exposed surface of an SPR-supporting material; and
    the pre-determined wavelength of the light from the light source is a function of the resonant wavelength of the SPR-supporting material.

9. The sensor of claim 8, wherein the pre-determined wavelength of the light from the light source is a function of the thickness of said coating of the SPR-supporting material.

10. The sensor of claim 8, wherein the pre-determined wavelength of the light from the light source is a function of the optical properties of the material of said SPR element.

11. The sensor of claim 10, wherein the pre-determined wavelength of the light from the light source is a function of the refractive index of the material of said SPR element.

* * * * *